United States Patent [19]
Lawson et al.

[11] Patent Number: 5,912,343
[45] Date of Patent: Jun. 15, 1999

[54] TERTIARY AMINES CONTAINING SIDE-CHAIN ORGANOLITHIUM STRUCTURES AND METHOD FOR THE PREPARATION THEREOF

[75] Inventors: David F. Lawson, Uniontown; William L. Hergenrother, Akron; Michael L. Kerns, Elyria, all of Ohio

[73] Assignee: Bridgestone Corporation, Tokyo, Japan

[21] Appl. No.: 08/777,657

[22] Filed: Dec. 31, 1996

[51] Int. Cl.$^6$ ...................... C07D 207/06; C07D 211/18; C07D 223/04; C07D 225/02

[52] U.S. Cl. ................... 540/450; 540/581; 540/582; 540/477; 540/611; 540/612; 546/133; 546/112; 546/184; 546/192; 548/577; 548/578; 548/579

[58] Field of Search ..................... 540/450, 581, 540/582, 477, 611, 612; 546/133, 192; 548/577

[56] References Cited

U.S. PATENT DOCUMENTS

| | | | |
|---|---|---|---|
| 3,109,871 | 11/1963 | Zalinski | 260/85.1 |
| 3,178,398 | 4/1965 | Strobel | 260/85.1 |
| 3,639,367 | 2/1972 | Halasa | 260/85.1 |
| 4,550,142 | 10/1985 | Akita | 525/236 |
| 4,734,461 | 3/1988 | Roggero | 525/293 |
| 4,735,994 | 4/1988 | Roggero | 525/279 |
| 4,935,471 | 6/1990 | Halasa | 525/359.1 |
| 5,066,729 | 11/1991 | Stayer, Jr. | 525/315 |
| 5,112,929 | 5/1992 | Hall | 526/181 |
| 5,153,159 | 10/1992 | Antkowiak | 502/155 |
| 5,332,810 | 7/1994 | Lawson | 540/450 |
| 5,496,940 | 3/1996 | Lawson | 540/450 |
| 5,523,364 | 6/1996 | Engel et al. | 526/180 |
| 5,527,753 | 9/1996 | Engel | 502/155 |
| 5,550,203 | 8/1996 | Engel et al. | 526/336 |
| 5,567,815 | 10/1996 | Hall | 540/541 |
| 5,574,109 | 11/1996 | Lawson | 525/280 |
| 5,605,872 | 2/1997 | Engel et al. | 502/157 |
| 5,626,798 | 5/1997 | Schwindeman et al. | 260/665 |
| 5,663,398 | 9/1997 | Schwindeman et al. | 556/466 |
| 5,718,877 | 2/1998 | Manev et al. | 423/599 |
| 5,726,308 | 3/1998 | Hall et al. | 540/484 |
| 5,736,617 | 4/1998 | Kerns et al. | 525/354.2 |
| 5,786,441 | 7/1998 | Lawson et al. | 528/229 |

FOREIGN PATENT DOCUMENTS

| | | |
|---|---|---|
| 0207559 | 6/1986 | European Pat. Off. . |
| 0212693 | 6/1986 | European Pat. Off. . |
| 0316255 | 10/1988 | European Pat. Off. . |

OTHER PUBLICATIONS

Cram and Hammond, "Organic Chemistry" pp. 565–567 (1964) McGraw Hill Book Co, New York.
"Preparation of Some Triakyl Tin–Lithium compounds", *J. Am. Chem. Soc.* 75, Gillman et al., 2507–2509, (1953).
"Preparation and Reactions of Trialkyltinlithium", by Tamborski et al., pp. 237–239, (1963).
"An Improved Synthesis of p–dimethylaminophenyl–lithium", by Hallas and Waring, *Chemistry and Industry*, p. 620, (May 1969).
Riddick et al., *Organic Solvents*, 3rd Edition, Wiley–Inter. Science, N.Y., pp. 52–53, (1970).
"Functionally Substituted Organolithium Compounds. The Lithium Derivatives of Dimethylbenzylamines", C.T., by Viswanathan et al., *J. Organometallic Chem.*, pp. 1–7, 54, (1973).
"Anionic Polymerization VII. Polymerization and Copolymerization with Lithium Nitrogen Bonded Initiator", by Cheng, *American Chem. Soc.*, pp. 513–528, (1981).
"Lithiation of N,N–diamethylmethallylamine", by Fitt et al., *J. Org. Chem.* 46, pp. 3349–3352, (1981).
D.H. Richards, D.M Service and M.J. Stewart, *Brit. Polym. J. 16*, p. 117, (1984).
"Styrene–Butadiene Rubbers", by Henderson, *Rubber Technology*, 3rd Ed., Van Nostrand Reinhold, N.Y., pp. 228–233, (1987).
P. Charlier, R. Jerome and P. Teyssie, *Macromolecules No. 23*, p. 1831, (1990).
K. Ueda, A. Hirao and S. Nakahama, *Macromolecules No. 23*, p. 939, (1990).
*British Polymer J. 22*, pp. 319–325, (1990).
"Recent Advances in Anionic Synthesis of Functionalized Elastomers Using Functionalized Alkyllithium Initiators" by Quirk et al., *Rubber Chemistry and Technology*, vol. 69, pp. 444–461, (1996).
"Anionic Polymerization of Dienes Using Homogeneous Lithium Amide (N–Li) Initiators", by Lawson et al., *Polymer Preprints*, 37(2), pp. 728–729, (1996).

*Primary Examiner*—John M. Ford
*Attorney, Agent, or Firm*—Daniel N. Hall

[57] ABSTRACT

A compound comprising at least one cyclic amine, having an organolithium side-chain, defined according to formula (I)

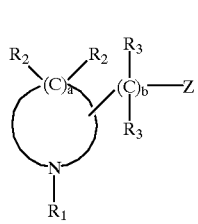

(I)

wherein Z is a lithium atom (Li); $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members.

19 Claims, No Drawings

TERTIARY AMINES CONTAINING SIDE-CHAIN ORGANOLITHIUM STRUCTURES AND METHOD FOR THE PREPARATION THEREOF

TECHNICAL FIELD

The present invention generally relates to anionic initiators and polymers made using anionic initiators. Specifically, the anionic initiators are organolithium compounds. More specifically, the anionic initiators are cyclic amines having an organolithium side-chain moiety. Polymers prepared with the compounds of the present invention exhibit improved characteristics including improved compounding stability, improved hysteresis loss characteristics, and reproducible, relatively narrow range, molecular weight distributions.

BACKGROUND OF THE INVENTION

When conducting polymerizations on a commercial basis, it is important to utilize process conditions and components which will allow the molecular weight of the end products to be narrowly and reproducibly defined. The characteristics of a given polymer and its usefulness are dependent, among other things, upon its molecular weight. Hence, it is desirable to be able to predict with some certainty the molecular weight of the end product of the polymerization. When the molecular weight is not narrowly definable, or is not reproducible on a systematic basis, the process is at a commercial disadvantage.

Further, it is desirable to produce elastomeric compounds exhibiting improved properties such as reduced hysteresis loss characteristics. Such elastomers, when compounded to form articles such as tires, power belts and the like, will show an increase in rebound, a decrease in rolling resistance and less heat build-up when mechanical stresses are applied.

A major source of hysteretic power loss has been established to be due to the section of the polymer chain from the last cross link of the vulcanizate to the end of the polymer chain. This free end cannot be involved in an efficient elastic recovery process, and as a result, any energy transmitted to this section of the cured vulcanizate is lost as heat. It is known in the art that this type of mechanism can be reduced by preparing higher molecular weight polymers which will have fewer end groups. However, this procedure is not useful because processability of the rubber with compounding ingredients and during shaping operations decreases rapidly with increasing molecular weight of the rubber.

The present invention provides polymers made by anionic initiation with novel alkyllithium compounds containing cyclic amines. Use of the compounds of the present invention allows the incorporation of a functionality from the initiator to be incorporated at least at the head of the polymer chain. The initiators used in the invention not only provide for improved polymerizations, but also result in polymers having a relatively predictable, controllable and reproducible molecular weight range distribution. Because of the incorporated functionality, the polymers and products of the invention exhibit improved (that is, reduced) hysteresis loss characteristics.

Certain aminoalkyllithium compounds are known in the art. For example, U.S. Pat. No. 4,935,471 discloses dialkylamino oligoalkenyl lithiums including piperidinyl and pyrrolidinyl oligoalkenyl lithiums. It has been found that when compounded with conventional vulcanizable rubber components, some of these materials do not interact effectively with carbon black. Others possess an odor which makes their commercial use undesirable. U.S. Pat. No. 5,496,940 teaches organolithium compounds containing a cyclic amino group. These compounds contain a lithium alkyl moiety that is bonded to the amino nitrogen. The polymers resulting from these initiators have the amino group tethered through the nitrogen.

SUMMARY OF INVENTION

It is therefore, an object of the present invention to provide anionic polymerization initiators.

It is a further object of the present invention to provide a method of preparing anionic polymerization initiators.

It is still a further object of the invention to provide initiators that will reproducibly result in a polymer having a narrow, predictable molecular weight range.

It is an additional object of the invention to provide initiators that will allow for the incorporation of a functional group at least at the head of the resulting polymer.

It is another object of the present invention to provide methods of using such polymerization initiators to form improved elastomers.

It is yet another object of the present invention to use such initiators to provide elastomers having a plurality of polymer molecules wherein substantially each polymer has a functional group from the initiator.

It is also an object of certain embodiments of the present invention to provide anionic initiators that will produce diene polymers and copolymers capable of forming vulcanizates having reduced hysteresis characteristics.

It still a further object of the present invention to provide polymers having a substantial fraction of living organolithium chain ends adaptable to further functionalization or coupling.

It is yet another object of the present invention to provide initiators that are useful at higher polymerization temperatures than known amino-lithium initiators.

It is still another object of the present invention to provide amino-functionalized polymers having a decreased potential of losing the amino functionality.

It yet still another object of the present invention to provide polymers having a functional group with improved thermal stability.

It is also an object of the present invention to provide polymers having an amino-functional group that does not regenerate into a secondary amino species upon decomposition.

It is still another object of the present invention to provide polymers and vulcanizates thereof with improved interaction with carbon black and that do not have the objectionable odor associated with the piperidinyl and pyrrolidinyl compounds.

At least one or more of these objects together with the advantages thereof over the existing art, which shall become apparent from the specification which follows, are accomplished by the invention as hereinafter described and claimed.

In general, the present invention provides a compound comprising: at least one cyclic amine, having an organolithium side-chain, defined according to formula (I)

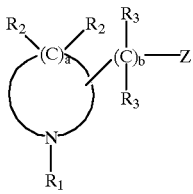

wherein Z is a lithium atom (Li); $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members.

The present invention further provides a process for preparing a cyclic amine having an organolithium side-chain comprising the steps of: reacting a cyclic amine, having an organohalide side-chain, defined according to formula (I)

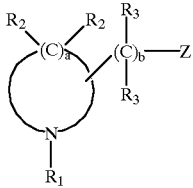

with a lithio reactant; wherein Z is a halide; $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members.

PREFERRED EMBODIMENT FOR CARRYING OUT THE INVENTION

As will become apparent from the description that follows, the present invention provides novel cyclic amine molecules, and compounds thereof, having an organolithium side-chain. The molecules are useful for, among other things, anionic polymerization initiators for the preparation of polymers, including copolymer elastomers. These novel molecules, and compounds thereof, will simply be referred to as initiators for purposes of this disclosure.

It has been discovered that certain polymers formed using initiators of the present invention exhibit useful properties, including reproducible, relatively narrow molecular weight ranges. Furthermore, these polymers contain a functionality from the initiator, which functionality is useful in reducing hysteresis loss characteristics in the resulting elastomeric compounds.

Another advantage provided by use of the initiators of the present invention is that the amine functionality becomes strongly tethered to the polymer chain, and is therefore less likely to become separated from the polymer during compounding operations wherein vulcanizable elastomeric compounds are formed. Subsequent to vulcanization, the desired reduction in hysteresis loss possessed by the compound is thereby insured as loss of amine functionality is minimized, if not substantially eliminated. Hysteresis loss reductions of at least 10 to 20 percent, and higher, are useful and obtainable by practice of the present invention.

Throughout this application, reference will be made to the variable Z. Based on the embodiment being discussed, Z will be defined in a manner consistent with that embodiment, and therefore, Z should be interpreted in view of each different embodiment. Inasmuch as one embodiment of the present invention deals with anionic polymerization initiators containing lithium, Z will be defined as lithium (Li). In view of the embodiment teaching the formation of an anionic polymerization initiator, Z will be defined as a halide. Likewise, where the specification is directed toward a living polymer having at its head a polymerization initiator moiety of the present invention, Z will be defined as a polymer having a lithium atom at its living or growing end. Similarly, where the present invention teaches a polymer, wherein the polymerization has been quenched or terminated with a functional unit, Z will be defined as a polymeric segment with an optional functional group at its terminal or tail end.

The initiator of the present invention contains a cyclic organo amine having an organolithium functionality branching from one of at least four carbon atoms within the cyclic amine ring. For purposes of this disclosure, the organolithium functionality, which branches from one of at least four carbon atoms, will be referred to as the organolithium side-chain. Specifically, cyclic organo amines of the present invention can be defined by the formula (I)

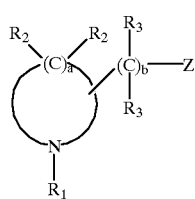

where Z is a lithium atom (Li); $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members. It should be appreciated that each $R_2$ and $R_3$ are of the same scope with the exception that $R_2$ can provide a bridging bond, however, $R_3$ is preferably hydrogen or a short organic group containing from 1 to about 3 carbon atoms.

With reference to formula (I), it should be understood that the amino ring can contain up to 16 ring carbon atoms in addition to the ring nitrogen, thereby forming a 17 member ring. Further, the organolithium side-chain, or Z containing moiety, can be joined to the amino ring at any of the up to 16 carbon atoms within the ring. Those of ordinary skill in the art will appreciate that the attachment of the Z containing moiety will take the place of one of the $R_2$ substituents at the tethered carbon.

With reference to those substituents that are independently selected, it should be understood that each substituent is separately selected without reference to any other substituent. For example, where a is 4, seven of the $R_2$s can be hydrogen atoms while the eighth can be an ethyl moiety. Likewise, where b is 3, five of the $R_3$s can be hydrogen atoms while the sixth can be a methyl moiety.

Regarding the use of the bridging bond, it should be appreciated that compounds represented by formula (I) can include multi-cyclo compounds such as bicyclo and tricyclo compounds. It should be understood that two bridging bonds will contribute to the formation of a bridge between two ring members, i.e. two ring carbons or one ring carbon and the ring nitrogen. Where there is a direct bond between two ring members, it is believed, without wishing to be bound to any particular theory, that the $R_1$ and $R_2$ variables simply represent an electron contributed to the bridge, which is a direct bond between ring members. Where the bridge formed between ring members includes an organic group, it should be understood that $R_1$ and $R_2$ provide a bonding cite where the bridge is joined to the ring; again, probably via the contribution of an electron. In view of this teaching, the use of the term substituent, as it relates to $R_1$ and $R_2$, should be interpreted so as to include atoms, organic moieties and bonding cites or electrons.

As an example, two $R_2$ bridging bonds can form a bridge across the cyclic amino ring, and thereby create a bicyclo compound. This bridge between two ring carbons can include 0 carbon atoms, in which case there is a direct bond between ring carbons. The bridge can also include up to about 6 carbon atoms, in which case the bridge comprises an organic group. Those of ordinary skill in the art will understand that inasmuch as a $R_2$ substituent contributes to a bridge, it will no longer be available as a hydrogen or organic group extending from the ring.

It should also be understood that a bridge can be formed between the ring nitrogen and a ring carbon. Those of ordinary skill in the art will appreciate that this bridge will be formed between the $R_1$ associated with the nitrogen and a $R_2$ of a ring carbon. This bridge can contain 0 carbon atoms, in which case there is a direct bond between the ring nitrogen and the ring carbon, or up to 6 carbon atoms, in which case the bridge comprises an organic group. It should also be understood that the cyclic structure defined by formula (I) can include more than one bridge.

For example, the bicyclo compounds that are generally defined by formula (I) can more specifically be represented by formulas (II) and (III)

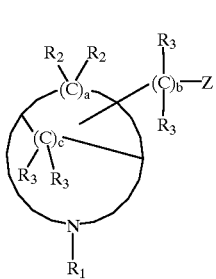

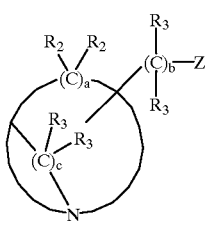

where the variables Z, $R_1$, $R_2$, $R_3$, a and b are as defined herein. Formula (II) represents a bicyclo compound wherein a bridge is formed between two ring carbons. The bridge length is defined by c, which is an integer between 0 and about 6. It should be appreciated that the Z containing moiety can extend from any carbon within the ring, including those carbons that may be in the bridge. Accordingly, it should also be understood that the Z containing moiety can be tethered to the bicyclo compound in the one ring, which contains the nitrogen, or in the adjacent ring. Formula (III) represents a bicyclo compound where a bridge is formed between the ring nitrogen and a ring carbon. The bridge length is again defined by c, which is an integer between 0 and about 6. As with formula (II), the Z containing moiety can extend from any of the carbon atoms within the ring, including those carbon atoms that may be in the bridge. It should be understood that the $R_1$ is not depicted in formula (III) inasmuch as it is part of the bridge. The same holds true for $R_2$, but each individual carbon, and associated $R_2$, is not represented in the formulas so as to facilitate depiction of the molecule.

The organic groups carbon-based moieties defined herein can contain unsaturation, but are preferably branched, straight chain, or cyclic alkyl groups. It should be further understood that the organic groups can contain hetero atoms including oxygen, sulfur and nitrogen. For example, the organic groups of the present invention can include tertiary amines, simple alkyl or alkenyl, cycloalkyl or cycloalkenyl, bicycloalkyl or bicycloalkenyl, or aralkyl groups, and their non-interfering oxygen, nitrogen, and sulfur containing analogs. Examples of such groups include dialkylaminos or dialkylaminoalkyls. Although the preceding examples of possible organic radical groups have been recited, the scope of the invention should not be limited thereto.

Some examples of the above defined initiators of the present invention are more specifically represented by the following formulae: (A), (B), (C), (D), (E), (F), (G), (H), (I), (J), (K), (L), (M), (N), (O), (P), (Q), (R), (S) and (T).

(A) 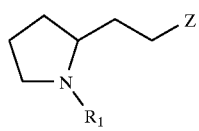
(B) 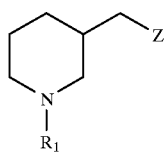
(C) 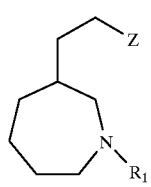
(D) 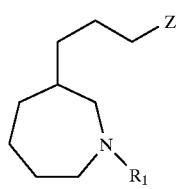
(E) 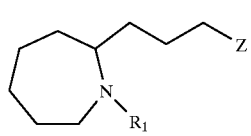
(F) 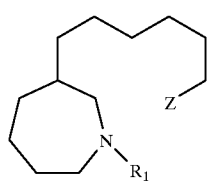
(G) 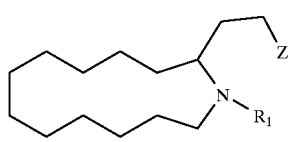
(H) 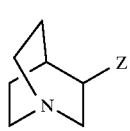
(I) 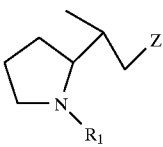
(J) 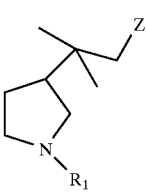
(K) 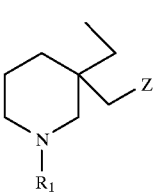
(L) 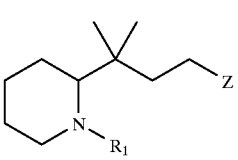
(M) 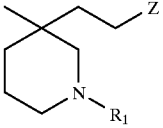
(N) 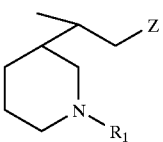
(O) 
(P) 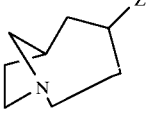
(Q) 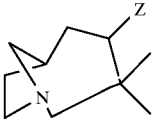

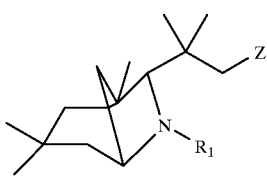
(R)

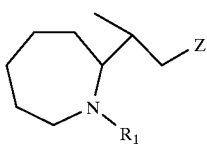
(S)

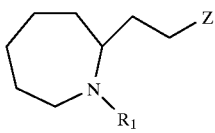
(T)

where Z is a lithium atom (Li); and $R_1$ is an organic group containing from about 1 to about 12 carbon atoms. Preferably, $R_1$ is an alkyl organic group, and most preferably is a methyl group.

With reference to the above formulae (A)-(T), when Z is Li and $R_1$ is a methyl group, it should be appreciated that formula (A) is a 2-(2-lithioethyl)-1-methylpyrrolidine. Likewise, the molecule represented by the formula (B) is a 3-(lithiomethyl)-1-methylpiperidine, and the molecule represented by the formula (H) is a 3-lithioquinuclidine. Formulae (A), (I) and (j) are pyrrolidine derivatives. Formulae (B) and (K) are piperidine derivatives. Formula (H), (O), (Q) and (R) are azabicyclooctane derivatives. Formula (P) is an azabicyclononane derivative. Formulae (C), (D), (E), (F), (L), (M), (N), (S) and (T) are tetrahydroazepine derivatives, and formula (G) is an azatridecane derivative. Formulae (A) and (B) are the most preferred of (A)-(T).

Other examples include various di-N-alkyl derivatives of piperazine (1,4-diazacyclohexane) and of di-N-alkylhomopiperazine (1,4-diazacyclo-heptanes). Another class of amines from which the aminoalkyllithiums may be derived includes various di-N-alkyl derivatives of 1,4-, or 1,5-diazacylooctanes, and ring C-substituted di-N-alkyl derivatives of 1,4-, or 1,5-diazacylooctanes, etc.

The initiator according to the present invention can be formed by a number of techniques, employing a variety of conditions, and using various hydrocarbon solvents, such as those used in the subsequently explained polymerizations. It should further be appreciated that the use of polar solvents may be necessary, alone or in conjunction with the hydrocarbon solvents, for improved solubility of the initiator reagent, provided that the solvents are compatible with anionic polymerizations and the solvent recovery and polymer drying procedures.

One preferred method of preparing an initiator compound according to the present invention is to react a cyclic amine compound having an organohalide side-chain extending from one of at least four carbon atoms within the ring, with a lithio reactant selected from elemental lithium metal, an organolithium compound, and mixtures thereof. In other words, a cyclic amine having an organohalide side-chain is reacted with at least about two molar equivalents of a reactant selected form the group consisting of elemental lithium metal and $R_5Li$ wherein $R_5$ is selected from the group consisting of alkyls, cycloalkyls, alkenyls, aryls and aralkyls having from 1 to about 20 carbon atoms and short chain length low molecular weight polymers from diolefin and vinyl aryl monomers having up to about 25 units.

The cyclic amine compound having an organohalide side-chain, which is a precursor for the preparation of the organolithium initiators defined above, can be defined according to formula (I) above, where Z is a halide; $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members. Chlorine and bromine are the preferred halides, with chlorine being most preferred. The organic groups are as defined hereinabove, and each $R_3$ is preferably hydrogen or a short organic group containing from 1 to about 3 carbon atoms.

It should be understood that the cyclic amine having an organohalide side-chain can also be represented by the formulas (A)-(T), where Z is a halide, chlorine being most preferred, and $R_1$ is as defined hereinabove.

An example of the method includes formation of the initiator 2-(2-lithioethyl)-1-methylpyrrolidine, which is useful for the production of reduced-hysteresis polymers in substantially hydrocarbon solvents, by the reaction of a mixture of one equivalent of 2-(2-chloroethyl)-1-methylpyrrolidine with at least about 2 atom equivalents of lithium metal. It should be appreciated that the preparation of cyclic amines having halide side-chains is known in the art.

When reacted with elemental lithium metal in a suitable solvent such as hexane, cyclohexane, benzene or the like, the resulting reduction reaction produces a lithiated cyclic amine compound wherein the lithium atom is directly bonded to a carbon atom or carbon chain branching from a carbon substituent within the amine ring. The lithiated cyclic amine compound can be complexed with one or more ligand molecules (such as THF), which help stabilize the molecule, but do not otherwise affect the reaction.

In the alternative, the cyclic amines having an organohalide side-chain can also be reacted with an organolithium reagent; this reaction taking place in a suitable solvent such as those described hereinabove. The organolithium reactant is defined by the formula $R_5Li$, wherein $R_5$ is an organic radical selected from the group consisting of alkyls, cycloalkyls, alkenyls, aryls and aralkyls having from 1 to about 20 carbon atoms, and short chain length low molecular weight polymers from diolefin and vinyl aryl monomers having up to about 25 units. Typical alkyls include n-butyl, s-butyl, t-butyl, methyl, ethyl, isopropyl and the like. Cycloalkyls include cyclohexyl, menthyl and the like. The alkenyls include allyl, vinyl, and the like. The aryl and aralkyl groups include phenyl, benzyl, oligo(styryl) and the like. Exemplary short chain length polymers include the oligo(butadienyls), oligo(isoprenyls), olio(styryls) and the like. Alkyllithium reactants such as t-butyllithium are preferred.

The two components are allowed to react for up to about 20 to 24 hours at moderate temperatures, preferably from about 0° C. to about 90° C. Reaction and post-treatment temperatures of from about 30° to about 70° C, are especially preferred.

If one atom equivalent of lithium in the organolithium reactant is used per atom equivalent of organohalide stemming from the cyclic amine, a by-product of the reaction will be an organohalide comprising the organic radical previously associated with the lithium, i.e. $R_5$, which may be undesirable for the intended use of the inventive compound. It is therefore, preferable to employ two or more atom equivalents of lithium from the organolithium reactant per atom equivalent of side-chain organohalide. It is believed that a reaction with the excess of lithium will result in a lithium halide and other low molecular weight hydrocarbon byproducts, which may be more acceptable for the intended use of the inventive initiator material.

For example, the preparation of 2-(2-lithioethyl)-1-methylpyrrolidine can be prepared in a "one-pot" generation by reacting 2-(2-chloroethyl)-1-methylpyrrolidine with two equivalents of t-butyllithium in situ. It should be appreciated that the initiators of this invention may optionally be treated with from about 1 to about 500 equivalents of a monomer, before the main copolymerization charge is made. Further, when successfully practiced, polymers of a narrow molecular weight distribution, with a substantial fraction of living C-Li chain ends adaptable to further functionalization or coupling, are obtained.

As stated above, the initiators of the present invention may be used to prepare any anionically-polymerizable polymer, e.g., homopolymers of polybutadiene, polyisoprene and the like, and copolymers thereof with monovinyl aromatics such as styrene, alpha methyl styrene and the like, or trienes such as myrcene, and mixtures of the foregoing. Suitable monomers include conjugated dienes having from about 4 to about 12 carbon atoms, monovinyl aromatic monomers having 8 to 18 carbon atoms and trienes. Examples of conjugated diene monomers and the like useful in the present invention include 1,3-butadiene, isoprene, 1,3-pentadiene, 2,3-dimethyl-1,3-butadiene and 1,3-hexadiene, and aromatic vinyl monomers include styrene, alpha-methylstyrene, p-methylstyrene, vinyltoluene and vinylnaphthalene. The conjugated diene monomer and aromatic vinyl monomer are normally used at the weight ratios of 95-50:5-50, preferably 95-65:5-35, respectively. Adducts of the initiator with monomers that do not homopolymerize, e.g. 1,1-diphenyl ethylene and substituted 1,1-diphenylethylenes, are also considered to be initiators of this invention.

Polymerization is conducted in polar or non-polar solvent, such as tetrahydrofuran (THF), a hydrocarbon solvent, such as the various cyclic and acyclic hexanes, heptanes, octanes, pentanes, their alkylated derivatives, and mixtures thereof. In order to promote randomization in copolymerization and to control vinyl content, a polar coordinator may be added to the polymerization ingredients. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed. Suitable polymerization modifiers include, for example, ethers or amines to provide the desired microstructure and randomization of the comonomer units. The molecular weight of the polymer ("base polymer") that is produced in this invention is optimally such that a proton-quenched sample will exhibit a gum Mooney (ML/4/100) of from about 1 to about 150. However, useful lower molecular weight compounds can also be made using these initiators. These might typically be considered fluids, having molecular weights ranging from several hundreds to tens of thousands of mass units. They can be used as viscosity modifiers and as dispersants for particulates, such as carbon black in oil.

Polymers of the present invention can be of any molecular weight, depending on the intended application. Generally, for purposes of making tire products, the molecular weight of the polymer should fall within the range from about 50,000 to about 1,000,000 preferably from 80,000 to about 500,000 and most preferably from about 100,000 to about 250,000. When used as a viscosity modifier, the molecular weight of the polymer should generally fall within the range from about 500 to about 50,000, preferably from about 1,500 to about 30,000 and most preferably from about 2,000 to about 15,000.

Other compounds useful as polar coordinators are organic and include tetrahydrofuran (THF), linear and cyclic oligomeric oxolanyl alkanes such as 2,2-bis (2'-tetrahydrofuryl) propane, di-piperidyl ethane, dipiperidyl methane, hexamethylphosphoramide, N-N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, owned by the Assignee of record, the subject matter of which relating to such modifiers is incorporated herein by reference. Compounds useful as polar coordinators include those having an oxygen or nitrogen hetero-atom and a non-bonded pair of electrons. Other examples include dialkyl ethers of mono and oligo alkylene glycols; "crown" ethers; tertiary amines such as tetramethylethylene diamine (TMEDA); linear THF oligomers; and the like.

A batch polymerization is begun by charging a blend of monomer(s) and normal alkane solvent to a suitable reaction vessel, followed by the addition of the polar coordinator (if employed) and the initiator compound previously described. The reactants are heated to a temperature of from about 20 to about 200° C., and the polymerization is allowed to proceed for from about 0.1 to about 24 hours. This reaction produces a reactive polymer having a lithium atom at the reactive or living end thereof.

Thus, substantially every resulting polymer molecule of the present invention can be represented by formula (I), hereinabove, where Z is living polymer chain having a lithium atom (Li) at its growing end; $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members. The organic groups are as defined hereinabove and each $R_3$ is preferably hydrogen or a short organic group containing from 1 to about 3 carbon atoms. The polymer is any anionically-polymerized polymer including, for example, those derived form diene homopolymers, monovinyl aromatic polymers, diene/monovinyl aromatic random copolymers and block copolymers.

For example, living polymers according to the formula (I) can be more specifically defined by formula (IV)

(IV)

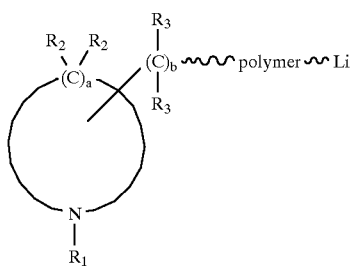

where $R_1$, $R_2$, $R_3$, a and b are as described hereinabove, and wherein the polymer can include any anionically-polymerized polymer. The organic groups and anionically-polymerized polymer is as described above.

It should be understood that the living polymer of the present invention can also be defined by formulas (A)-(T) wherein the Z is living polymer chain having a lithium atom (Li) at its reactive end, and $R_1$ is as defined hereinabove.

Further monomer addition at the living lithium end causes the molecular weight of the polymer to increase as the polymerization continues. To terminate the polymerization, and thus further control polymer molecular weight, a terminating agent, coupling agent or linking agent may be employed, all of these agents being collectively referred to herein as "terminating reagents". Termination of anionically polymerized living polymers having a lithium atom at a living end is well known in the art.

Accordingly, polymers according to the present invention can be defined by formula (I), hereinabove, where Z is a terminated polymer; $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members; and wherein the polymer can include any anionically-polymerized polymer. The polymer can be terminated by any known method or reagent known for terminating anionically polymerized living polymers. The polymer is as defined hereinabove, as are the organic groups, where $R_3$ is preferably hydrogen or a short organic group containing from 1 to about 3 carbon atoms.

The polymers of the present invention, such as defined by the formula (I), can more specifically be defined according to the formula (V)

(V)

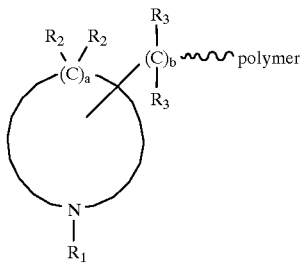

where $R_1$, $R_2$, $R_3$, a and b are as described above; and wherein the polymer can include any anionically-polymerized polymer. The polymer is as defined hereinabove, as are the organic groups, where $R_3$ is preferably hydrogen or a short organic group containing from 1 to about 3 carbon atoms. It should be appreciated that polymers according to the present invention can also be defined by formulas (A)-(T), where Z is a terminated polymer, and $R_1$ is as defined above.

Certain terminating reagents may provide the resulting polymer with a multifunctionality. That is, the polymers initiated according to the present invention may carry at least one amine functional group, which is a cyclic amine having a side-chain organo group that links the cyclic ring to the polymer, and may also carry a second functional group selected and derived from the group consisting of terminating reagents, coupling agents and linking agents.

Thus, the polymers of the present invention will include those defined by formula (I), hereinabove, where Z is a polymer containing a functional group, at the terminal or tail end of the polymer; $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members; and wherein the polymer can include any anionically-polymerized polymer. The polymer is as defined hereinabove, as are the organic groups, where $R_3$ is preferably hydrogen or a short organic group containing from 1 to about 3 carbon atoms.

For example, the polymer defined by formula (I) can be more specifically defined by the formula (VI)

(VI)

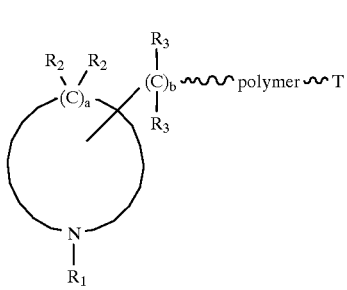

where $R_1$, $R_2$, $R_3$ a and b are as described above; T includes any functional group selected and derived from the group consisting of terminating reagents, coupling agents and linking agents; and wherein the polymer can include any anionically-polymerized polymer as defined above.

Preferably, T is an amine-containing functional group, and can be a cyclic amine having a side-chain organo group extending from a cyclic carbon substituent as described according to the present invention or an amino group formed by reaction with a terminating group that forms an amine, discussed hereinbelow. In other words, a preferred polymer according to the present invention will have a functional unit, as generally described by formula (I), at each extreme end of the polymer, one resulting from initiation, and the other resulting from termination. This multi-functionalized polymer can be described by formula (VII)

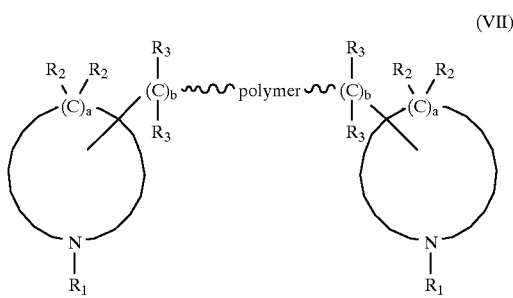

(VII)

where $R_1$ is selected from the group consisting of organic groups containing from 1 to about 12 carbon atoms and a bridging bond; each $R_2$ is independently selected from the group consisting of hydrogen, organic groups containing from 1 to about 12 carbon atoms, and a bridging bond; each $R_3$ is independently selected from the group consisting of hydrogen and organic groups containing from 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members; and wherein the polymer can include any anionically-polymerized polymer. The polymer is as defined hereinabove, as are the organic groups, where $R_3$ is preferably hydrogen or a short organic group containing from 1 to about 3 carbon atoms. See our copending application for further explanation of our terminators and terminated polymers entitled "Polymer, Elastomeric Compounds and Products Thereof, Terminated with Compounds Containing Side-Chain Amines." (Attorney Docket No. 9605025.)

Useful terminating reagents include active hydrogen compounds such as water or alcohol; carbon dioxide; toluene diisocyanate (TDI); N,N,N',N'-tetra-alkyldiamino-benzophenone, such as tetramethyidiamino-benzophenone or the like; N,N-dialkylamino-benzaldehyde, such asdimethylamino-benzaldehyde or the like; 1,3-dialkyl-2-imidazolidinones, such as 1,3-dimethyl-2-imidazolidinone (DMI) or the like; 1-alkyl substituted pyrrolidinones, such as N-methyl pyrrolidinone (NMP); 1-aryl substituted pyrrolidinones; dialkyl- and dicycloalkyl-carbodiimides having from about 5 to about 20 carbon atoms, such as 1,3-dicyclohexyl carbodiimide (DCCD); as well as the following:

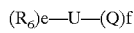

$(R_6)e\text{—}U\text{—}(Q)f$ where U is tin or silicon. It is preferred that U is tin. $R_6$ is an alkyl having from about 1 to about 20 carbon atoms; a cycloalkyl having from about 3 to about 20 carbon atoms; an aryl having from about 6 to about 20 carbon atoms; or, an aralkyl having from about 7 to about 20 carbon atoms. For example, $R_6$ may include methyl, ethyl, n-butyl, neophyl, phenyl, cyclohexyl or the like. Q is chlorine or bromine, "e" is from 0 to 3, and "f" is from about 1 to 4; where e+f=4.

Further, additional terminators include compounds expressed by the formulae

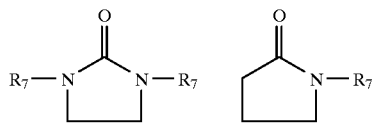

where each $R_7$ is the same or different and is an alkyl, cycloalkyl or aryl, having from about 1 to about 12 carbon atoms. For example, $R_7$ may include methyl, ethyl, nonyl, t-butyl, phenyl or the like. It should be appreciated that when $R_7$ is methyl, the above molecules are 1,3-dimethyl imidazolidinone (DMI) and N-methylpyrrolidine (NMP), respectively.

Additional terminators also include

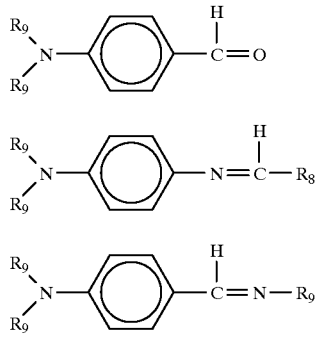

where $R_8$ is an alkyl, phenyl, alkylphenyl or dialkylaminophenyl, having from about 1 to about 20 carbon atoms. For example, $R_8$ may include t-butyl, 2-methyl-4-pentene-2-yl, phenyl, p-tolyl, p-butylphenyl, p-dodecylphenyl, p-diethyl-aminophenyl, p-(pyrrolidino) phenyl, and the like. Each $R_9$ is the same or different, and is an alkyl or cycloalkyl having from about 1 to about 12 carbon atoms. Two of the $R_9$ groups may together form a cyclic group. For example, $R_9$ may include methyl, ethyl, octyl, tetramethylene, pentamethylene, cyclohexyl or the like. When the $R_9$ groups are linked together as tetramethylene, it should be appreciated that the amino substituent is pyrrolidino.

Other examples of useful terminating reagents include tin tetrachloride, $(R_{10})_3SnCl$, $(R_{10})_2SnCl_2$, $R_{10}SnCl_3$, carbodiimides, cyclic amides, cyclic ureas, isocyanates, Schiff bases, 4,4'-bis(diethylamino) benzophenone, and the like, where $R_{10}$ is an alkyl, cycloalkyl or aralkyl having from 1 to about 12 carbon atoms, and other reactive hysteresis-reducing terminating compounds which may contain other heteroatoms such as oxygen, nitrogen, sulfur, phosphorus, tin, non-interfering halogen, etc. Suitable terminating reagents also include the isomeric vinylpyridines, other (bis)dialkylamino-benzophenones (e.g., Michler's ketone), etc. Exemplary amino groups formed by reaction with a terminating group that forms an amine includes any of the foregoing amine containing compounds, such as TDI, NMP, DMI, DCCD and the like.

When the living polymer is coupled with or end-linked with any of the various known coupling reagents, such as silicon tetrachloride, tin tetrachloride, etc., symmetrically "dicapped" polymers are prepared. When end-linking polymers through reaction with for example, $(R_5)_e SnQf$, $SnCl_4$, or $C_4H_9SnCl_3$ to obtain products with substantially greater than 10 percent/end-linking through tin, especially desirable elastomeric compositions with low hysteresis properties are prepared. $(R_5)_e SnQf$ is defined, where $R_5$ is selected from the group consisting of alkyls, cycloalkyls, alkenyls, aryls and aralkyls having from 1 to about 20 carbon atoms and short chain length low molecular weight polymers from diolefin and vinyl aryl monomers having up to about 25 units, and Q, e and f are as described hereinabove.

The terminating reagent is added to the reaction vessel, and the vessel is agitated for about 1 to about 1000 minutes. As a result, an elastomer is produced having an even greater affinity for compounding materials such as carbon black, and hence, even further reduced hysteresis. Additional examples of terminating reagents include those found in U.S. Pat. No. 4,616,069 which is herein incorporated by reference for the disclosure of terminating agents.

The polymer may be separated from the solvent by conventional techniques. These include steam or alcohol coagulation, thermal desolventization, or any other suitable method. Additionally, solvent may be removed from the resulting polymer by drum drying, extruder drying, vacuum drying or the like.

The elastomers made from the anionic initiators of the present invention comprise a plurality of polymer molecules, having a functional group at the head, and preferably also, at the tail of the resulting polymer. Conventional compounding of such elastomers with fillers, and subsequent curings results in products exhibiting reduced hysteresis, which means a product having increased rebound, decreased rolling resistance and having less heat build-up when subjected to mechanical stress.

The polymers made from the anionic initiators of the present invention can be used alone or in combination with other elastomers to prepare a product such as a tire treadstock, sidewall stock or other tire component stock compound. Such stocks are useful for forming tire components such as treads, subtreads, black sidewalls, body ply skims, bead fillers and the like. At least one such component is produced from a vulcanizable elastomeric or rubber composition. For example, they can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, poly(chloroprene), ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. When the polymers of the present invention are blended with conventional rubbers, the amounts can vary widely such as between 10 and 99 percent by weight of the former.

The polymers can be compounded with carbon black in amounts ranging from about 20 to about 100 parts by weight, per 100 parts of rubber (phr), with about 40 to about 70 phr being preferred. The carbon blacks may include any of the commonly available, commercially-produced carbon blacks but those having a surface area (EMSA) of at least 20 $m^2/g$ and more preferably at least 35 $m^2/g$ up to 200 $m^2/g$ or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following TABLE I.

TABLE I

| CARBON BLACKS | |
|---|---|
| ASTM Designation (D-1765-82a) | Surface Area $(m^2/g)$ (D-3765) |
| N-110 | 126 |
| N-220 | 111 |
| N-339 | 95 |
| N-330 | 83 |
| N-550 | 42 |
| N-660 | 35 |

The carbon blacks utilized in the preparation of the rubber compounds used may be in pelletized form or an unpelletized flocculent mass. Preferably, for more uniform mixing, unpelletized carbon black is preferred. The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology,* 3rd ed., Wiley Interscience, N.Y. 1982, Vol. 20, pp. 365–468, particularly "Vulcanization Agents and Auxiliary Materials" pp. 390–402. Vulcanizing agents may be used alone or in combination.

Vulcanizable elastomeric compositions made from the above elastomers can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology* 3rd ed., Wiley Interscience, N.Y. 1982, Vol. 20, pp. 365–468, particularly "Vulcanization Agents and Auxiliary Materials" pp. 390–402. Vulcanizing agents may be used alone or in combination. This invention does not affect cure times and thus the polymers can be cured for a conventional amount of time. Cured or crosslinked polymers will be referred to as vulcanizates for purposes of this disclosure.

GENERAL EXPERIMENTAL

In order to demonstrate the preparation and properties of the initiators according to the present invention and their use in anionic polymerization, a number of such cyclic amino side-chain alkyllithium compounds were prepared. These compounds were then used as initiators to form a number of elastomers.

The aminoalkyllithium reagents of the invention may be prepared under a variety of conditions, using various hydrocarbon solvents as discussed hereinabove. The reagents may be used in polymerizations using such polar or nonpolar solvents as may be necessary for improved solubility of the aminoalkyllithium reagent, provided that the solvents are compatible with anionic polymerizations and the solvent recovery and polymer drying procedures.

In one preferred embodiment of the invention that provides for the production of reduced hysteresis polymers in substantially hydrocarbon solvents, such as hexane or cyclohexane, the initiator is 2-(2-lithioethyl)-1-methyl pyrrolidine, which may be generated by at least two exemplary routes as is also discussed above: 1) by the reaction of a mixture of one equivalent of, for example, 2-(2-chloroethyl)-1-methyl pyrrolidine with about two atom equivalents of lithium metal; or 2) 2-(2-lithioethyl)-1-methyl pyrrolidine wherein 2-(2-chloroethyl)-1 -methyl pyrrolidine is treated with two equivalents of t-butyllithium. The reactions are preferably performed in hexanes, cyclohexane, benzene, or mixtures thereof.

For greatest stability, the initiator precursors employed in the present invention are usually handled as their hydrohalide or hydro-hydrogen sulfate salts, which are treated with base just prior to their use in forming the initiators, in order to liberate the free halo organo amines. This can be explained according to the following exemplary reaction.

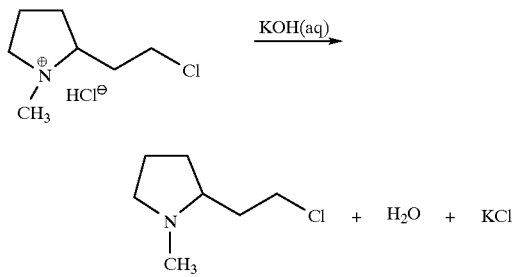

The amino alkyllithium reagents of the invention may be formed in a solvent or solvent mixture, and then transferred to another solvent or solvent mixture for use in a polymerization reaction.

The initiators of this invention may optionally be treated with from about one to 500 equivalents of a monomer such as butadiene or isoprene, before the main (co) polymerization charge is made, although this is not required. Polymers according to the invention can be prepared with a relatively narrow molecular weight range distribution, with a substantial fraction of living C-Li chain ends adaptable to further functionalization or coupling, being obtained.

The initiator formation, polymerization, and coupling and/or termination may be performed in one reaction vessel, or second or third reactor vessels, or transfer lines from the original reactor can be used, by introducing the preformed initiator to the monomer mixture, or vice-versa. Polymerization and post-treatment conditions should be used that avoid the introduction of air and/or protic or other reactive contaminants, such as moisture, etc., and prolonged heating or storage at excessive temperatures should be avoided unless the live ends are stabilized. Moderate temperatures (from about 0° C. to about 100° C.) are preferred for the polymerizations and the terminations, although higher or lower temperatures may be used. Polymerization and post-treatment temperatures of from about 30° C. to 70° C. are especially preferred. The polymerization time may vary from a few minutes to days, depending on the temperature, solvent and presence of any donor solvent, the monomer structures, and the molecular weight desired.

Any suitable method for isolation of the terminated rubber or fluid may be used, for example: quenching with water, steam, an acid or an alcohol (these may be introduced during the desolventization step), and desolventization by drum drying, coagulation in alcohol, water or steam, extruder drying, vacuum drying, spray drying or any combination thereof. Desolventization by drum-drying, coagulation in alcohol, steam or hot water desolventization, extruder drying, vacuum drying, spray drying or combinations thereof are preferred. An antioxidant and/or antiozonant compound is usually added to the polymer or polymer cement at or before this stage. In most of the experimental examples of this invention, alcohol coagulation followed by drum-drying or vacuum drying were used.

Upon drying, the elastomers are compounded in a carbon black-filled test stock (see Low-Oil Test Recipe, TABLE II), and the physical properties determined in comparison to those of related base polymers without the modifications. In practice, a wide variety of compounding recipes may be used to give favorable results with this invention, although hysteresis properties may vary from formulation to formulation, depending on the type and amount of carbon black and oil used, and so on. Certain other fillers, such as silica or hydrated silica may also be used. Furthermore, the polymers made with the initiators of this invention may be combined in proportions of 20 to 100 percent by weight with 80 to 0 percent by weight of other polymers to give elastomeric compositions with reduced hysteresis loss characteristics. The low molecular weight products made from the initiators of this invention may be used at low levels to influence the properties of mixtures with other fluids and/or particulates.

TABLE II

LOW-OIL TEST FORMULATION FOR EVALUATION OF HYSTERESIS

| Ingredient | Mix Order | Parts per Hundred Parts of Rubber |
|---|---|---|
| Polymer | 1 | 100 |
| Naphthenic oil | 2 | 10 |
| Carbon black, N-351 | 3 | 55 |
| ZnO | 4 | 3 |
| Antioxidant | 5 | 1 |
| Wax blend | 6 | 2 |
| Total Masterbatch: | | 171 |
| Stearic acid | | 2 |
| Sulfur | | 1.5 |
| Accelerator | | 1 |
| Total Final: | | 175.5 |

Masterbatch: 145°–155° C., 60 RPM
(drop after 5 min, @ 155°–175° C.)
Final: 77° to 95° C., 40 RPM

EXAMPLE 1

A "one pot" preparation of 2-(2-lithioethyl)-1-methylpyrrolidine.

2-(2-chloroethyl)-1 -methylpyrrolidine was dissolved in cyclohexane and reacted with about two molar equivalents of t-butyllithium in pentane in an inert atmosphere including argon or nitrogen. The resulting mixture was agitated gently at room temperature for about an hour. The mixture was allowed to stand overnight and used to initiate the polymerization of butadiene and styrene as described in the following examples.

EXAMPLE 2

A "one pot" preparation of 3-lithiomethyl-1-methylpiperidine

Following the general procedure set forth in Example 1 hereinabove, 3-lithiomethyl-1-methylpiperidine was prepared from 3-chloromethyl-1-methylpiperidine.

EXAMPLE 3

Polymerization of styrene/butadiene mixtures using 2-(2-lithioethyl)-1-methylpyrrolidine A polymerization was run using the initiator solution prepared according to Example 1 hereinabove. TABLE Ill, hereinbelow, lists the ingredients and conditions used in the polymerization to produce Sample A. A 0.113 M solution of the above initiator was added to a dried, sealed, nitrogen-purged bottle, through a Viton rubber cap liner, to a 75 percent/25 percent by weight blend of butadiene and styrene in hexanes, at an estimated level of 0.85 milliequivalent ("meq.") active C-Li/100 grams monomer, and an additional amount of N,N,N',N'-tetramethyl ethylenediamine ("TMEDA") was added at the TMEDA/Li ratio indicated in TABLE Ill, hereinbelow.

The mixtures were agitated at 50° C. for 0.5 to 2.5 hours "hr", proceeding to approximately 94–98 percent conversion to polymer. In practice, there is considerable leeway in the reaction times and temperatures, much the same as there is leeway in the reaction vessels, type of agitation, etc., used. The treated cements then were quenched by injection with 1.5 ml of i-PrOH (isopropyl alcohol), treated with an antioxidant (3 ml of a mixture containing 1.6 wt% dibutyl paracresol (DBPC) in hexane), coagulated in i-PrOH, air-dried at room temperature, then drum-dried. Suitable characterization tests were performed. Analyses of the product polymer are given in TABLE IV (Run A), hereinbelow.

EXAMPLE 4

Polymerization of styrene/butadiene mixtures using 3-lithiomethyl-1-methylpiperidine and end-linking with SnCl$_4$ The procedure of Example 3 was followed employing the initiator of Example 2, except that after 150 minutes of polymerization at 50° C., the polymerization mixture was treated with 0.8 equivalent of SnCl$_4$ per equivalent of Li charged. Table III, Sample B, hereinbelow, lists the ingredients and conditions used in the polymerization to form Sample 8. The mixture was agitated at 50° C. for 30 minutes. The product was isolated and dried in the same manner as above. It showed greater than about 50 percent coupling in the 50° C. polymerization. Analyses of this polymer are also given in TABLE IV (Sample B), hereinbelow.

TABLE III

POLYMERIZATION OF STYRENE/BUTADIENE

| | SAMPLE A | SAMPLE B |
|---|---|---|
| Amount (g) of Monomer | 83.2 | 74.6 |
| ml of 1.02 M TMEDA (TMEDA/Li) | 0.31 | 0.28 |
| Initiator, meq. | 0.53 | 0.49 |
| Initiator, ml | 4.71 | 4.34 |
| Pzm temperature, ° C. | 50 | 50 |
| Pzm time, minutes | 150 | 150 |

TABLE IV

ANALYSIS OF POLYMERS

| | A | B |
|---|---|---|
| Polymer recovered % | 93 | 83 |
| Tg, ° C. (DSC, onset) | −40 | −31 |
| Chain-bound amine, mol % | 69 | 78 |
| GPC (THF): | | |
| Mn | 135000 | 280000 |
| M$_w$/M$_n$ | 1.14 | 1.48 |
| $^1$H NMR | | |
| Styrene wt % | 25.5 | 25.7 |
| Block Styrene wt % | 1.4 | — |
| 1,2- wt % | 35.8 | 41.2 |
| 1,4- wt % | 38.7 | 33.1 |

EXAMPLE 5

Compounded evaluations of polymers made from anionic initiators of the present invention The product polymers (from Samples A and B of Table IV) were compounded and tested as indicated in the test recipe shown in TABLE II, and cured 20 min @ 165° C. Compared to the control polymer, the results of the compounded evaluations are summarized in TABLE V. The control polymer, C, consisted of a tin control polymer, (a tin-coupled styrene/butadiene rubber ("SBR") initiated with n-butyllithium). Similar to the control polymer, the polymer product of Sample A exhibited comparably improved hysteresis loss characteristics and enhanced interaction with carbon black, as compared to unmodified elastomers of the same molecular weight embodied in the control polymer. In these experiments, the polymers were of higher molecular weight than anticipated, since the initiator was part of a mixture.

TABLE V

POLYMER ANALYSIS

| Polymer Sample | Feature | ML/4-Cpd | Dynastat 1 Hz, tan δ 50° C. |
|---|---|---|---|
| A | 2-(2-lithioethyl)-1-methylpyrrolidine, I, H-termination | 106 | 0.120 |
| B | 3-lithiomethyl-1-methyliperidine, II, SnCl$_4$ coupling | 133 | 0.136 |
| C | Sn-Coupled control (BuLi initiator) | 88 | 0.126 |

It is clear from the foregoing examples and specification disclosure, that the present invention provides novel cyclic aminolithium compounds useful for example, as anionic polymerization initiators for the preparation of polymers. Reproducible polymerization of such polymers within a relatively narrow molecular weight range is achieved, and the resulting polymers also exhibit good preservation of live C-Li ends which permits further polymer functionalization through the use of terminating reagents.

It is to be understood that the invention is not limited to the specific initiator reactants, monomers, terminators, polar coordinators or solvents disclosed herein, except as otherwise stated in the specification. Similarly, the examples have been provided merely to demonstrate practice of the subject invention and do not constitute limitations of the invention. Those skilled in the art may readily select other monomers and process conditions, according to the disclosure made hereinabove. Also, it should be understood that formula (I) is a generic formula, encompassing all formulae described herein within its scope.

Thus, it is believed that any of the variables disclosed herein can readily be determined and controlled without departing from the scope of the invention herein disclosed and described. Moreover, the scope of the invention shall include all modifications and variations that fall within the scope of the attached claims.

What is claimed is:

1. A cyclic amine compound selected from the compounds of formula (I):

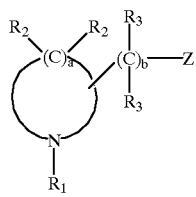

(I)

wherein Z is a lithium atom (Li); $R_1$ is selected from the group consisting of moieties of 1 to about 12 carbon atoms and a bridging bond; each $R_2$ is independently selected from the group consisting of hydrogen, moieties of 1 to about 12 carbon atoms, and a bridging bond: each $R_x$ is independently selected from the group consisting of hydrogen and moieties of 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members, wherein one or more of said carbon atoms in said moieties may be replaced by oxygen, sulfur, or nitrogen, and where said moieties may contain unsaturation or multiple unsaturation.

2. A compound, as set forth in claim 1, where $R_3$ is independently selected from the group consisting of hydrogen and moieties of 1 to about 3 carbon atoms, wherein one or more of said carbon atoms in said moieties may be replaced by oxygen, sulfur, or nitrogen, and where said moieties may contain unsaturation or multiple unsaturation.

3. A compound, as set forth in claim 1, where $R_2$ and $R_3$ are selected from hydrogen and alkyl groups, and $R_1$ is an alkyl group.

4. A compound, as set forth in claim 1, wherein said cyclic amine is selected from the group consisting of tetrahydroazepine derivatives, azatridecane derivatives, pyrrolidine derivatives, piperidine derivatives, azabicyclooctane derivatives, and azabicyclononane derivatives.

5. A compound, as set forth in claim 4, wherein said cyclic amine is 2-(2-2 lithioethyl)-1 -methylpyrrolidine.

6. A compound, as set forth in claim 4, wherein said cyclic amine is 3-2 (lithioethyl)-1-methylpiperidine.

7. A compound, as set forth in claim 4, wherein said cyclic amine is a 3-2 lithioquinuclidine.

8. A process for preparing a cyclic amine having an organolithium side-chain comprising the steps of:

reacting a cyclic amine, having an organohalide side-chain, defined according to formula (I)

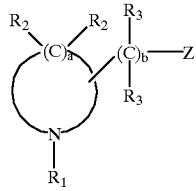

(I)

wherein Z is a lithium atom (Li); $R_1$ is selected from the group consisting of moieties of 1 to about 12 carbon atoms and a bridging bond; each $R_2$ is independently selected from the group consisting of hydrogen, moieties of 1 to about 12 carbon atoms, and a bridging bond; each $R_3$ is independently selected from the group consisting of hydrogen and moieties of 1 to about 12 carbon atoms; a is an integer from 4 to about 16; and b is an integer from 0 to about 12; and optionally including a bridge, formed by the selection of two of said bridging bonds, the bridge having 0 to about 6 carbon atoms between the bridging ring members, wherein one or more of said carbon atoms in said moieties may be replaced by oxygen, sulfur, or nitrogen, and where said moieties may contain unsaturation or multiple unsaturation.

9. A process for preparing a cyclic amine having an organolithium side-chain, according to claim 8, wherein said lithio reactant is selected from elemental lithium metal, an organolithium compound, and mixtures thereof.

10. A process for preparing a cyclic amine having an organolithium side-chain, according to claim 9, wherein said organolithium compound is defined by the formula $R_5Li$ is selected from the group consisting of alkyls, cycloalkyls, alkenyls, aryls, and aralkyls having from 1 to about 20 carbon atoms and short chain length low molecular weight polymers from diolefin and vinyl aryl monomers having up to about 25 units.

11. A process for preparing a cyclic amine having an organolithium side-chain, according to claim 8 wherein $R_3$ is hydrogen or moieties of 1 to about 3 carbon atoms, wherein one or more of said carbon atoms in said moieties may be replaced by oxygen, sulfur, or nitrogen, and where said moieties may contain unsaturation or multiple unsaturation.

12. A process for preparing a cyclic amine having an organolithium side-chain, according to claim 8, where $R_2$ and $R_3$ are selected from hydrogen and alkyl groups, and $R_1$ is an alkyl group.

13. A process for preparing a cyclic amine having an organolithium side-chain, according to claim 8, wherein said cyclic amine is selected from the group consisting of tetrahydroazepine derivatives, azatridecane derivatives, pyrrolidine derivatives, piperidine derivatives, azabicyclooctane derivatives, and azabicyclononane derivatives.

14. A process for preparing a cyclic amine having an organolithium side-chain, according to claim 8, wherein said cyclic amine is a 2-(2-chloroethyl)-1-methylpyrrolidine.

15. A process for preparing a cyclic amine having an organolithium side-chain, according to claim 8, wherein said cyclic amine is a 3-(chloroethyl-1-methylpiperidine.

16. A process for preparing a cyclic amine having an organolithium side-chain, according to claim 8, wherein said cyclic amine is a 3-chloroquinuclidine.

17. A compound, as set forth in claim 4, wherein said cyclic amine is selected from the group consisting of

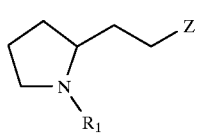 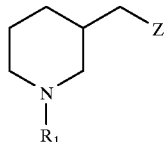

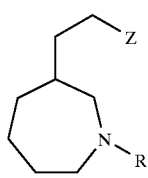 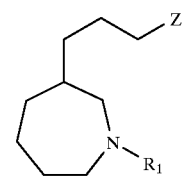

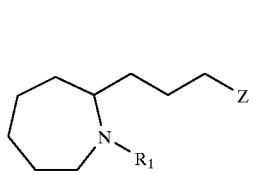 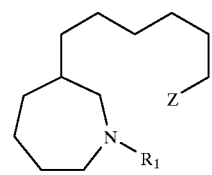

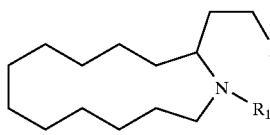 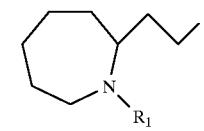

where Z is a lithium atom, and $R_1$ is an alkyl group having from 1 to about 12 carbon atoms.

18. A compound, as set forth in claim 4, wherein said cyclic amine is selected from the group consisting of

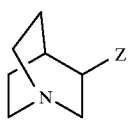 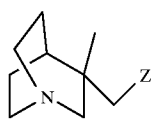 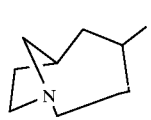

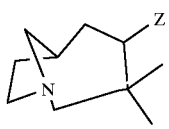

where Z is a lithium atom.

19. A compound, as set forth in claim 4, wherein said cyclic amine is selected from the group consisting of

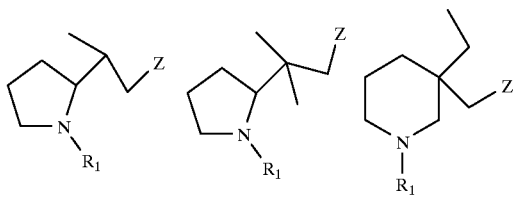

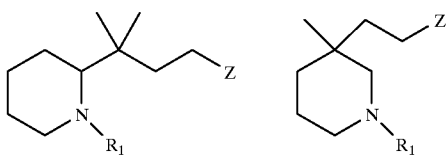

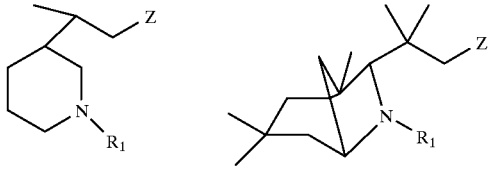

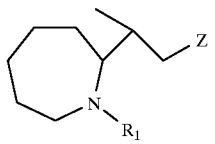

where Z is a lithium atom, and $R_1$ is an alkyl group having from 1 to about 12 carbon atoms.

* * * * *

UNITED STATES PATENT AND TRADEMARK OFFICE
CERTIFICATE OF CORRECTION

PATENT NO : 5,912,343
DATED : 6/15/99
INVENTOR(S): David F. Lawson, et al.

It is certified that error appears in the above-identified patent and that said Letters Patent is hereby corrected as shown below:

Column 23, line 40: "$R_x$" should read -- $R_3$ --.

Column 24, line 2: "3-2 lithioquinuclidine" should read -- 3-lithioquinuclidine --.

Signed and Sealed this

Twenty-eighth Day of November, 2000

Attest:

Q. TODD DICKINSON

*Attesting Officer*   *Director of Patents and Trademarks*